United States Patent [19]
Burkhart et al.

[11] Patent Number: 5,560,814
[45] Date of Patent: Oct. 1, 1996

[54] USE OF THIOURONIUM SALTS AS BRIGHTENERS FOR AQUEOUS ACIDIC ELECTRONICKELIZATION BATHS

[75] Inventors: Bernd Burkhart, Mutterstadt; Alfred Oftring, Bad Durkheim; Volker Schwendemann, Neustadt; Ulrich Schroeder, Frankenthal; Klaus Glaser, Mannheim, all of Germany

[73] Assignee: BASF Aktiengesellschaft, Ludwigshafen, Germany

[21] Appl. No.: 454,156

[22] PCT Filed: Dec. 2, 1993

[86] PCT No.: PCT/EP93/03383

§ 371 Date: Jun. 15, 1995

§ 102(e) Date: Jun. 15, 1995

[87] PCT Pub. No.: WO94/13862

PCT Pub. Date: Jun. 23, 1994

[30] Foreign Application Priority Data

Dec. 15, 1992 [DE] Germany ............ 42 42 194.2

[51] Int. Cl.$^6$ ............... C25D 3/12; C25D 3/16
[52] U.S. Cl. ............ 205/271; 205/274; 205/275; 205/280
[58] Field of Search ............ 205/246, 255, 205/271, 274, 275, 280; 558/5

[56] References Cited

U.S. PATENT DOCUMENTS

| | | | |
|---|---|---|---|
| 2,892,760 | 6/1959 | Gundel et al. | 205/271 |
| 3,630,857 | 12/1971 | Du Rose et al. | 204/49 |
| 3,721,581 | 3/1973 | Teramura et al. | 558/5 |
| 3,882,009 | 5/1975 | Wagener et al. | 204/181 |

FOREIGN PATENT DOCUMENTS

| | | |
|---|---|---|
| 0193303 | 9/1986 | European Pat. Off. . |
| 1191652 | 4/1965 | Germany . |

OTHER PUBLICATIONS

Protection of Metals, vol. 27, No. 2, Mar./Apr. 1991, pp. 258–261, A. S. Milushkin, et al., "Using New Thiourea Derivatives as Brighteners in Nickel Plating."

*Primary Examiner*—Kathryn Gorgos
*Assistant Examiner*—Edna Wong
*Attorney, Agent, or Firm*—Oblon, Spivak, McClelland, Maier & Neustadt, P.C.

[57] ABSTRACT

Nickel-plated shaped parts are produced by galvanic precipitation of nickel from aqueous-acid baths which contain as essential constituents one or several nickel salts, one or several inorganic acids and one or several brighteners. As brighteners are used thiourea salts having general formula (I), in which $R^1$ to $R^4$ stand for hydrogen, $C_1$ to $C_{18}$-alkyl, which may be substituted by carboxyl groups, $C_1$ to $C_4$-alkoxycarbonyl groups or cyano groups, $C_2$ to $C_{12}$-alkenyl, $C_2$ to $C_{12}$-alkinyl, $C_5$ to $C_8$-cycloalkyl, $C_7$ to $C_{12}$-phenylalkyl or phenyl, which may be substituted by one or two $C_1$ to $C_4$-alkyl residues, $C_1$ to $C_4$-alkoxy residues, halogen atoms, hydroxyl groups, phenyl groups, phenyl residues or $C_1$ to $C_4$ alkoxycarbonyl groups; Y sands for a chemical bond or for linear or branched alkylene, alkenylene or alkinylene having each up to 20 C. atoms; A stands for hydrogen or a group having the formulae: —CO—H, —CO—$R^5$, —CO—OH, —CO—O$R^5$, —CO—N$R^6R^7$, —CO—$CH_2$—CO—O$R^5$, —O—CO—H, —O—CO—$R^5$, —N$R^6$—CO—$R^5$, —N$R^6$—CO—$R^5$, —O$R^5$, —$SO_2$—$R^5$, —$SO_2$—OH, —$SO_2$—O$R^5$, —PO(PH)$_2$, —PO(OH)(O$R^5$), —PO(O$R^5$)$_2$, OPO(OH)$_2$, —OPO(PH)(P$R^5$) or —OPO(O$R^5$)$_2$ in which $R^5$ stands for $C_1$ to $C_{12}$-alkyl, $C_2$ to $C_{12}$-alkenyl, $C_2$ to $C_{12}$-alkinyl, $C_5$ to $C_8$-cycloalkyl, $C_7$ to $C_{12}$-phenylalkyl or phenyl, which may be substituted by one or two $C_1$ to $C_4$-alkyl residues, halogen atoms, hydroxyl groups, phenyl residues or $C_1$ to $C_4$-alkoxycarbonyl groups; and $R^6$ and $R^7$ stand for hydrogen or $C_1$ to $C_4$-alkyl; n is a number from 1 to 4 and $X_{(-)}$ stands for s water solubility-promoting, n-valent inorganic or organic anion.

11 Claims, No Drawings

USE OF THIOURONIUM SALTS AS BRIGHTENERS FOR AQUEOUS ACIDIC ELECTRONICKELIZATION BATHS

The present invention relates to a process for producing nickelized shaped articles by electrodeposition of nickel from aqueous acidic baths using thiouronium salts as brighteners. The invention also relates to those thiouronium salts which are novel compounds.

It is also known that acidic nickel electrolytes must contain small amounts of organic substances if the electronickelization is to produce a bright, ductile and level deposition of the metal. Such brighteners, which in general are divided into primary and secondary brighteners, are customarily used in the form of combinations comprising a plurality of these agents in order to enhance the effect.

Praktische Galvanotechnik, Eugen G. Lenze Verlag, Saulgau, 4th edition 1984, pages 268 to 271 (1) describes customary brighteners for nickel electrolytes. Although the compounds are classified as primary or secondary brighteners or leveling agents, it is admitted at the same time that clear-cut classification is not always possible. The brightening compounds mentioned are:

sulfonimides, e.g. benzoic sulfimide sulfonamides benzenesulfonic acids, e.g., mono-, di- and tribenzenesulfonic acid naphthalenesulfonic acids, e.g., mono-, di- and trinaphthalenesulfonic acid alkylsulfonic acids sulfinic acid arylsulfone sulfonates aliphatic compounds with ethylene and/or acetylene bonds, e.g., butynediol single- and multi-ring nitrogen-containing heterocycles with or without further hetero atoms such as sulfur or selenium coumarin amines and quaternary ammonium compounds as leveling agents saccharin.

DE-B-1 191 652 (2) describes single- or multi-ring heterocyclic nitrogen bases of the aromatic type in quaternized form such as pyridinium salts, e.g. 2-(1-pyridinio)ethanesulfate, as levelers, ie. brighteners, for acidic nickel-plating baths. These agents are used together with customary basic brighteners such as benzene-m-disulfonic acid, diaryldisulfimides or sulfonamides.

U.S. Pat. No. 3,630,857 (3) discloses using nitrile group-containing thiourea derivatives of the general formula

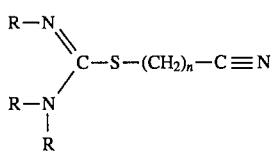

where the Rs are independently of one another hydrogen, alkyl, alkenyl or alkynyl each of from 1 to 4 carbon atoms and n is from 1 to 4, as brighteners for aqueous acidic electronickelization baths.

In commercial practice, it is customary to combine alkenylsulfonic acids such as sodium vinylsulfonate or sodium allylsulfonate with other brighteners such as propargyl alcohol, 2-butyne-1,4-diol, propynesulfonic acid or 3-(1-pyridinio)-1-propanesulfonate.

However, the prior art agents generally need to be used in relatively high concentrations in the nickel electrolyte baths used.

It is an object of the present invention to provide an improved process for producing nickelized shaped articles using brighteners that are superior or at least equal in brightening to, for example, 2-(1-pyridinio)ethanesulfate or 3-(1-pyridinio)-1-propanesulfonate, but can be used in a lower concentration.

We have found that this object is achieved by a process for producing nickelized shaped articles by electrodeposition of nickel from aqueous acid baths containing as essential constituents one or more nickel salts, one or more inorganic acids and one or more brighteners, which comprises using as brighteners thiouronium salts of the general formula I

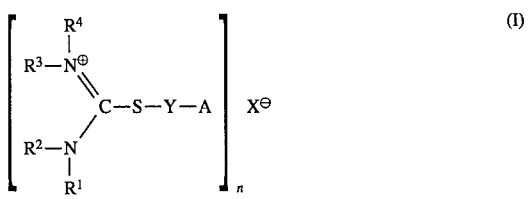

where $R^1$ to $R^4$ are each hydrogen, $C_1$–$C_{18}$-alkyl, which may be carboxyl-, $C_1$–$C_4$-alkoxycarbonyl- or cyano-substituted, $C_2$–$C_{12}$-alkenyl, $C_2$–$C_{12}$-alkynyl, $C_5$–$C_8$-cycloalkyl, $C_7$–$C_{12}$-phenylalkyl or phenyl which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl, Y is a chemical bond or linear or branched alkylene, alkenylene or alkynylene having in each case up to 20 carbon atoms, A is hydrogen or a group of the formula —CO—H, —CO—$R^5$, —CO—OH, —CO—$OR^5$, —CO—$NR^6R^7$, —CO—$CH_2$—CO—$OR^5$, —O—CO—H, —O—CO—$R^5$, —$NR^6$—CO—$R^5$, —$OR^5$, —$SO_2$—$R^5$, —$SO_2$—OH, —$SO_2$—$OR^5$, —PO(OH)$_2$, —PO(OH)($OR^5$), —PO($OR^5$)$_2$, OPO(OH)$_2$, —OPO(OH)($OR^5$) or —OPO($OR^5$)$_2$, where $R^5$ is $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl which may be substituted by one or two substituents selected from the group consisting of $C_1$–$C_4$-alkyl, halogen, hydroxyl, phenyl and $C_1$–$C_4$-alkoxycarbonyl, and $R^6$ and $R^7$ are each hydrogen or $C_1$–$C_4$-alkyl, n is from 1 to 4, and $X^\ominus$ is an n-valent inorganic or organic anion that promotes solubility in water.

Suitable $C_1$–$C_4$-alkyl for $R^6$ to $R^{10}$, $R^{12}$ and $R^{13}$ and for substituents on phenyl are n-propyl, isopropyl, n-butyl, isobutyl, sec-butyl, tert-butyl and in particular methyl and ethyl.

Examples of straight-chain or branched $C_1$–$C_{18}$- or $C_1$–$C_{12}$-alkyl for $R^1$ to $R^4$, $R^5$ and ($R^{11}$) in addition to the abovementioned $C_1$–$C_4$-alkyl radicals are n-amyl, isoamyl, sec-amyl, tert-amyl, neopentyl, n-hexyl, n-heptyl, n-octyl, 2-ethylhexyl, n-nonyl, isononyl, n-decyl, n-undecyl, n-dodecyl, n-tetradecyl, n-hexadecyl and n-octadecyl. Of these, $C_1$–$C_4$-alkyl is preferred.

Examples of suitable carboxyl-, $C_1$–$C_4$-alkoxycarbonyl- or cyano-substituted $C_1$–$C_{18}$-alkyl for $R^1$ to $R^4$ are 2-carboxyethyl, 2-(methoxycarbonyl)ethyl, 2-(ethoxycarbonyl)ethyl and 2-cyanoethyl.

Suitable $C_5$–$C_8$-cycloalkyl for $R^1$ to $R^4$, $R^5$ and $R^{11}$ is in particular cyclopentyl, cyclohexyl, cycloheptyl, cyclooctyl, methylcyclopentyl, dimethylcyclopentyl, methylcyclohexyl, dimethylcyclohexyl or ethylcyclohexyl. Of these, preference is given to cyclopentyl and cyclohexyl.

Examples of suitable $C_7$–$C_{12}$-phenylalkyl for $R^1$ to $R^4$, $R^5$ and $R^{11}$ are 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 6-phenylhexyl and in particular benzyl.

In monosubstituted phenyl for $R^1$ to $R^4$, $R^5$ and $R^{11}$ the substitution pattern is ortho, meta or preferably para and in disubstituted phenyl the substituents are preferably in the 2,4-position, for example as in 2,4-xylyl. If substituents are present, the degree of substitution is preferably 1. But particular preference is given to unsubstituted phenyl.

Suitable $C_1$–$C_4$-alkoxy radicals are in particular methoxy and ethoxy but also n-propoxy, n-butoxy, isobutoxy, sec-butoxy and tert-butoxy.

Examples of $C_1$–$C_4$-alkoxycarbonyl are n-propoxycarbonyl, isopropoxycarbonyl, n-butoxycarbonyl, isobutoxycarbonyl, sec-butoxycarbonyl, tert-butoxycarbonyl but in particular ethoxycarbonyl and methoxycarbonyl.

The term halogen atom herein encompasses fluorine, iodine and in particular bromine and especially chlorine.

Examples of straight-chain or branched $C_2$–$C_{12}$-alkylene for $R^1$ to $R^4$, ($R^5$ and $R^{11}$) are vinyl, allyl, methallyl, 3-butenyl, 4-pentenyl, 5-hexenyl, 7-octenyl, 9-decenyl, 11-dodecenyl, citronellolyl, geraniolyl and linaloolyl.

Examples of suitable straight-chain or branched $C_2$–$C_{12}$-alkynyl for $R^1$ to $R^4$, $R^5$ and $R^{11}$ are ethynyl and 2-propynyl.

$R^6$ to $R^{10}$, $R^{12}$ and $R^{13}$ are each preferably hydrogen, methyl or ethyl.

m is preferably from 0 to 8, in particular from 0 to 5, especially from 0 to 3.

Suitable n-valent anions X are the customary, normally water-solubilizing inorganic or organic anions, in particular chloride, bromide, fluoride, sulfate, hydrogensulfate, methanesulfonate, trifluoromethanesulfonate, 2-hydroxyethanesulfonate, p-toluenesulfonate, nitrate, tetrafluoroborate, perchlorate, 1-hydroxyethane-1,1-diphosphonate, dihydrogenphosphate, hydrogen phosphate, phosphate, formate, acetate, oxalate, citrate and tartrate.

Of these, anions with one or two charges (n=1 or 2) are preferred, in particular fluoride, sulfate, methanesulfonate, nitrate and tetrafluoroborate but especially chloride and bromide.

If A is a carboxylic acid, sulfonic acid, phosphonic acid or phosphoric acid function, the thiouronium salts I can also be present as betaines which can be formed by elimination of HX from the thiouronium salts I.

A preferred embodiment comprises using thiouronium salts I wherein $R^1$ to $R^4$ are each hydrogen, $C_1$–$C_4$-alkyl, allyl or phenyl which may be substituted by one or two $C_1$–$C_4$-alkyl radicals. In particular, $R^1$ to $R^4$ are all hydrogen or three hydrogens and one allyl.

In a further preferred embodiment, the thiouronium salts used have the general formula Ia

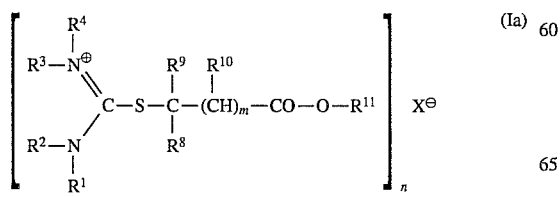

where $R^1$ to $R^4$, n and $X^\ominus$ are each as defined above, $R^8$ to $R^{10}$ are each hydrogen or $C_1$–$C_4$-alkyl, $R^{11}$ is hydrogen, $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl which may be substituted by one or two $C_1$–$C_4$-alkyl radicals, and m is from 0 to 10.

In a further preferred embodiment, the thiouronium salts have the general formula Ib

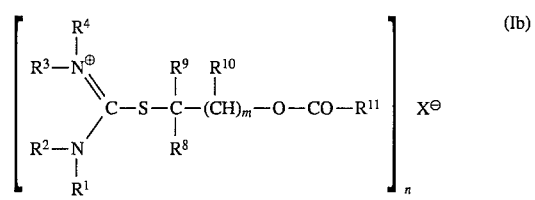

where $R^1$ to $R^4$, $R^8$ to $R^{11}$, m, n and $X^\ominus$ are each as defined above.

In a further preferred embodiment, the thiouronium salts have the general formula Ic

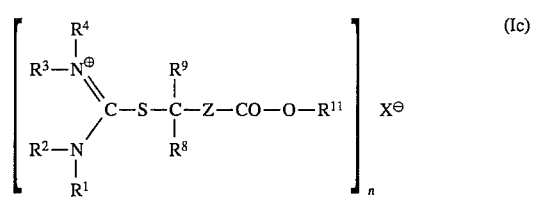

where $R^1$ to $R^4$, $R^8$, $R^9$, $R^{11}$, n and $X^\ominus$ are each as defined above and Z is a group of the formula —$CR^{12}$=$CR^{13}$— or —C≡C— where $R^{12}$ and $R^{13}$ are each hydrogen or $C_1$–$C_4$-alkyl.

In a further preferred embodiment, the thiouronium salts have the general formula Id

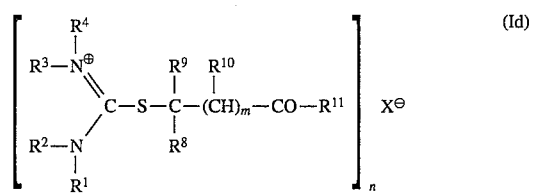

where $R^1$ to $R^4$, $R^8$ to $R^{11}$, m, n and $X^\ominus$ are each as defined above.

In a further preferred embodiment, the thiouronium salts have the general formula Ie

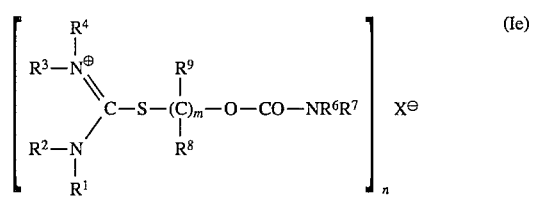

where $R^1$ to $R^4$, $R^6$ to $R^9$, m, n and $X^\ominus$ are each as defined above.

In a further preferred embodiment, the thiouronium salts have the general formula If

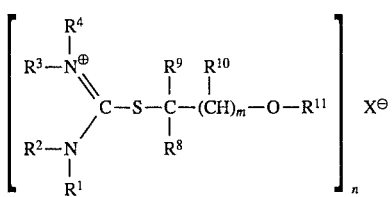

where
R$^1$ to R$^4$, R$^8$ to R$^{11}$, m, n and X$^\ominus$ are each as defined above.

In a further defined embodiment, the thiouronium slats have the general formula Ig

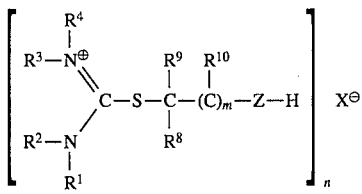

where
R$^1$ to R$^4$, R$^8$, R$^9$, Z, m, n and X$^\ominus$ are each as defined above.

Since the thiouronium salts I act in a way that is typical of secondary brighteners, they are preferably used combined with at least one further, normally primary brightener or else, as the case may be, with one or more further secondary brighteners. Examples of suitable primary brighteners are sodium vinylsulfonate and sodium allylsulfonate, and examples of suitable secondary brighteners are 2-butyne-1, 4-diol or propargyl alcohol.

The aqueous acidic nickel electrolyte baths used contain one or usually more than one nickel salt, for example nickel sulfate and nickel chloride, one or more inorganic acids, preferably boric acid and sulfuric acid, as brighteners the compounds I alone or preferably combined with further, customary brighteners and optionally further customary auxiliaries and additives in the concentrations customary therefor, for example wetting agents and pore inhibitors. Customary aqueous acidic nickel electrolytes ("Watts electrolytes") have the following basic composition:

200–300 g/l of NiSO$_4$.7 H$_2$O
30–150 g/l of NiCl$_2$.6 H$_2$O
30–50 g/l of H$_3$BO$_3$.

The electrolyte bath pH is customarily within the range from 3 to 6, preferably within the range from 4 to 5. This pH is conveniently set with a strong mineral acid, preferably sulfuric acid.

The compounds I are present in the electrolyte baths in low concentrations, in general within the range from 0.01 to 0.5 g/l, preferably within the range from 0.025 to 0.3 g/l. The concentrations of further, customary brighteners are in each case normally within the range from 0.1 to 10 g/l, in particular from 0.1 to 2.0 g/l.

The nickel electrolyte baths described can be used to electroplate in particular nickel coatings onto shaped articles made of steel, but also onto shaped articles made of other materials, for example brass, which have been pretreated as usual. The electroplating is in general carried out at from 30° to 80° C., preferably at from 40° to 60° C.

The compounds I of the invention are notable for extremely powerful brightening. In general they produce better brightness than the customary brighteners and, what is more, usually at a distinctly lower concentration in the nickel electrolyte baths.

The thiouronium salts I described are advantageously preparable by reacting the corresponding precursor of the general formula II Nuc-Y-a (II)

where Nuc is a nucleofugic leaving group, preferably chlorine or bromine, with a thiourea of the general formula III

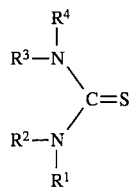

and, if desired, subsequently exchanging the anion Nuc$^\ominus$ for X$^\ominus$.

Suitable thioureas III include for example unsubstituted thiourea, N-methylthiourea, N,N'-dimethylthiourea, N,N,N', N'-tetramethylthiourea, N-ethylthiourea, N,N'-diethylthiourea, N,N,N',N'-tetraethylthiourea, N-phenylthiourea, N,N'-diphenylthiourea, N-phenyl-N-methylthiourea, N-phenyl, N'-methylthiourea, N,N'-dibutylthiourea, N-benzylthiourea, N-allylthiourea or N,N'-dicyclohexylthiourea.

The reaction of components II and III is advantageously carried out in an inert organic solvent such as toluene, xylene, petroleum ether, naphtha, cyclohexane, acetone, tetrahydrofuran, dioxane, methanol, ethanol, isopropanol, ethyl acetate or methyl benzoate or in a mixture thereof. However, the reaction can also be carried out in water or in a single-phase or two-phase mixture of water and one or more organic solvents, preferably polar organic solvents. In the case of two-phase mixtures it is possible to use a customary phase transfer catalyst. The reaction is generally carried out at from 40° to 130° C., in particular at from 60° to 110° C., and at atmospheric pressure.

Since some of the thiouronium salts I are novel substances, the present invention also relates to these novel compounds.

The present invention accordingly provides thiouronium salts of the general formula Ih

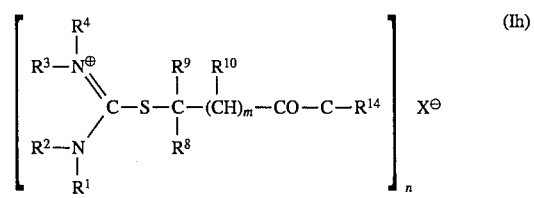

where
R$^1$ to R$^4$, R$^8$ to R$^{10}$, m, n and X$^\ominus$ are each as defined above and R$^{14}$ is C$_7$–C$_{12}$-phenylalkyl or phenyl which may be substituted by one or two C$_1$–C$_4$-alkyl radicals.

The present invention further provides thiouronium salts of the general formula Ij

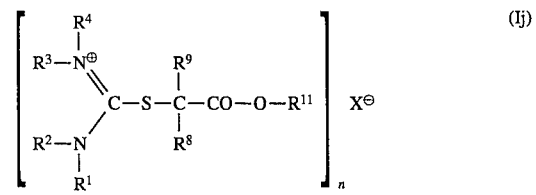

where
R$^1$ to R$^4$, R$^8$, R$^9$, R$^{11}$, n and X$^\ominus$ are each as defined above, subject to the proviso that at least one of R$^8$ and R$^9$ is not hydrogen.

The present invention further provides thiouronium salts of the general formula Ib

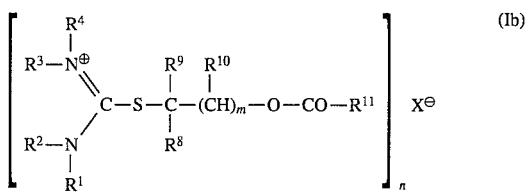

(Ib)

where

R$^1$ to R$^4$, R$^8$ to R$^{11}$, m, n and X$^\ominus$ are each as defined above.

The present invention further provides thiouronium salts of the general formula Ik

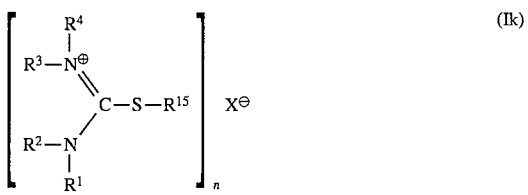

(Ik)

where

R$^1$ to R$^4$, n and X$^\ominus$ are each as defined above and R$^{15}$ is the group

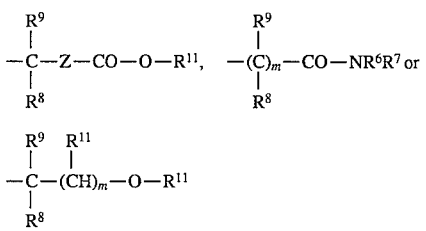

where

R$^6$ to R$^{11}$, Z and m are each as defined above, subject to the proviso that at least one of R$^1$ to R$^4$ is allyl.

The thiouronium salts Ih and Ij are subgroups of the compounds Ia and the thiouronium salts Ik are subgroups of the compounds Ic, Ie and If. At the same time, the use of the thiouronium salts Ih, Ij and Ik in the novel process for producing nickelized shaped articles is in each case a further preferred embodiment.

Preparation Examples

EXAMPLE 1

Preparation of 2-(benzyloxycarbonylmethyl)thiouronium chloride 7.6 g (0.1 mol) of thiourea were dissolved in 50 ml of acetone. 18.5 g (0.1 mol) of benzyl chloroacetate were added dropwise and the mixture was heated at the boil for two hours. After cooling down to room temperature, the precipitated product was filtered off and washed with diethyl ether. Drying left 23.5 g (corresponding to a yield of 90%) of the title compound in the form of colorless crystals. The product was more than 99% pure.

EXAMPLE 2

Preparation of 2-(1-carboxypropyl)thiouronium bromide

Example 1 was repeated with thiourea and 2-bromobutyric acid, affording the title compound in a yield of 79%.

EXAMPLE 3

Preparation of 2-(2-carboxy-2-propyl)thiouronium chloride

Example 1 was repeated with thiourea and 2-chloro-2-methylpropionic acid, affording the title compound in a yield of 74%.

EXAMPLE 4

Preparation of 2-(N,N-dimethylcarbamoylmethyl)thiouronium chloride

Example 1 was repeated with thiourea and 2-chloro-N,N-dimethylacetamide, affording the title compound in a yield of 89%.

EXAMPLE 5

Preparation of 2-(4-oxopentyl)thiouronium chloride

Example 1 was repeated with thiourea and 3-chloropropyl methyl ketone, affording the title compound in a yield of 71%.

EXAMPLE 6

Preparation of N-allyl-S-(N,N-dimethylcarbamoylmethyl)thiouronium chloride

Example 1 was repeated with N-allylthiourea and 2-chloro-N,N-dimethylacetamide, affording the title compound in a yield of 79%.

EXAMPLE 7

Preparation of N-allyl-S-(2-methoxyethyl)thiouronium bromide

Example 1 was repeated with -allylthiourea and 2-bromoethyl methyl ether, affording the title compound in a yield of 69%.

EXAMPLE 8

Preparation of N-allyl-S-(3-carboxy-2-butenyl)thiouronium bromide

Example 1 was repeated with N-allylthiourea and 4-bromo-2-methylcrotonic acid, affording the title compound in a yield of 70%.

Use Examples

The products prepared in Examples 1 to 8 were used as brighteners in weakly acidic electroplating baths for the deposition of nickel.

The aqueous nickel electrolyte used had the following composition:

300 g/l of NiSO$_4$.7 H$_2$O 60 g/l of NiCl$_2$.6 H$_2$O

45 /l of H$_3$BO$_3$ 2 g/l of saccharin 0.8 g/l of vinylsulfonic acid, sodium salt x g/l of brightener as per table 0.5 g/l of a fatty alcohol derivative of the formula C$_{12}$H$_{25}$/C$_{14}$H$_{29}$—O—(CH$_2$CH$_2$O)$_2$—SO$_3$Na as wetting agent.

The pH of the electrolyte was set to 4.2 with sulfuric acid.

Brass panels were used. Prior to being coated with nickel they had been cathodically degreased in a conventional manner in an alkaline electrolyte. They were nickelized in a 250 ml Hull cell at 55° C. with a current strength of 2A over a period of 10 minutes. The panels were then rinsed with water and dried over compressed air.

The table below shows the results of these experiments. It can be seen that the brighteners of the invention produced better brightness than the prior art brighteners, in some instances at a distinctly lower concentration in the nickel electrolyte bath.

TABLE

Test results of electronickelization

| Example No. | Brightener | Concentration | Brightness |
|---|---|---|---|
| 9 | of Example No. 1 | 0.1 | 5 |
| 10 | of Example No. 2 | 0.2 | 5 |
| 11 | of Example No. 3 | 0.2 | 5 |
| 12 | of Example No. 4 | 0.2 | 5 |
| 13 | of Example No. 5 | 0.2 | 5 |
| 14 | of Example No. 6 | 0.2 | 5 |
| 15 | of Example No. 7 | 0.2 | 5 |
| 16 | of Example No. 8 | 0.3 | 5 |
| for comparison | | | |
| A | 2-(1-pyridinio)-ethanesulfate | 0.3 | 4–5 |
| B | 3-(1-pyridinio)-propanesulfonate | 0.3 | 4–5 |

Rating scheme for brightness:
5 = excellent (perfect specular gloss)
4 = good (almost specular gloss)
3 = moderate
2 = poor
1 = no brightness
Comparative compound A is known from (2).
Concentration: [g/l]

We claim:

1. A process for producing nickelized shaped articles by electrodeposition of nickel from an aqueous acidic bath containing one or more nickel salts, one or more inorganic acids and one or more brighteners, which comprises using as brighteners thiouronium salts of formula I

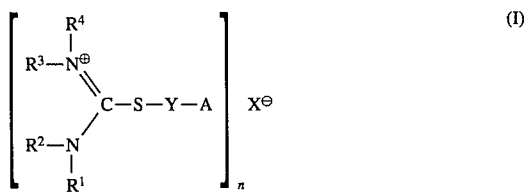

where $R^1$ to $R^4$ are each hydrogen, $C_1$–$C_{18}$-alkyl, which may be carboxyl-, $C_1$–$C_4$-alkoxycarbonyl- or cyano-substituted, $C_2$–$C_{12}$-alkenyl, $C_2$–$C_{12}$-alkynyl, $C_5$–$C_8$-cycloalkyl, $C_7$–$C_{12}$-phenylalkyl or phenyl which may be substituted by one or two substituents selected from the group consisting of $C_1$–$C_4$-alkyl, $C_1$–$C_4$-alkoxy, halogen, hydroxyl, phenyl and $C_1$–$C_4$-alkoxycarbonyl, Y is a chemical bond or linear or branched alkylene, alkenylene or alkynylene having in each case 1 to 20 carbon atoms, A is hydrogen or a group of the formula —CO—H, —CO—$R^5$, —CO—OH, —CO—$OR^5$, —CO—$NR^6R^7$, —CO—$CH_2$—CO—$OR^5$, —O—CO—H, —O—CO—$R^5$, —$NR^6$—CO—$R^5$, —$OR^5$, —$SO_2$—$R^5$, —$SO_2$—OH, —$SO_2$ —$OR^5$, —PO(OH)($OR^5$), or —PO($OR^5$)$_2$, where $R^5$ is $C_1$–$C_{12}$-alkyl, $C_2$–$C_{12}$-alkenyl, $C_2$–$C_{12}$-alkynyl, $C_5$–$C_8$ -cycloalkyl, $C_7$–$C_{12}$-phenylalkyl or phenyl which may be substituted by one or two substituents selected from the group consisting of $C_1$–$C_4$-alkyl, halogen, hydroxyl, phenyl and $C_1$–$C_4$-alkoxycarbonyl, and $R^6$ and $R^7$ are each hydrogen or $C_1$–$C_4$-alkyl, n is from 1 to 4, and $X^\ominus$ is an n-valent inorganic or organic anion that promotes solubility in water.

2. The process of claim 1, wherein A is selected from the group consisting of —CO—H, —CO—$R^5$, —CO—OH, —CO—$OR^5$, —CO—$NR^6R^7$, —CO—$CH_2$—CO—$OR^5$, —O—CO—H, —O—CO—$R^5$, —$NR^6$—CO—$R^5$, and —$OR^5$.

3. The process of claim 1 wherein $R^1$ to $R^4$ are each hydrogen, $C_1$–$C_4$-alkyl, allyl or phenyl which may be substituted by one or two $C_1$–$C_4$-alkyl radicals.

4. The process of claim 1, wherein said thiouronium salt has formula Ia

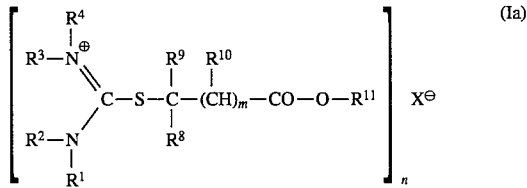

where $R^1$ to $R^4$, n and $X^\ominus$ are each as defined above, $R^8$ to $R^{10}$ are each hydrogen or $C_1$–$C_4$-alkyl, $R^{11}$ is hydrogen, $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl which may be substituted by one or two $C_1$–$C_4$-alkyl radicals, and m is from 0 to 10.

5. The process of claim 1, wherein said thiouronium salt has formula Ib

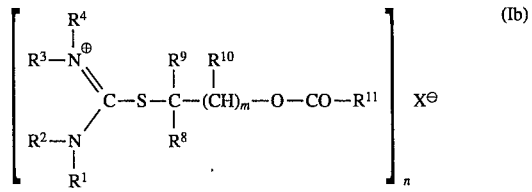

where $R^1$ to $R^4$, n and $X^\ominus$ are each as defined above, $R^8$ to $R^{10}$ are each hydrogen or $C_1$–$C_4$-alkyl, $R^{11}$ is hydrogen, $C_1$–$C_{12}$-alkyl, $C_2$–$C_{12}$-alkenyl, $C_2$–$C_{12}$-alkynyl, $C_5$–$C_8$-cycloalkyl, $C_7$–$C_{12}$-phenylalkyl or phenyl which may be substituted by one or two $C_1$–$C_4$-alkyl radicals, and m is from 0 to 10.

6. The process of claim 1, wherein said thiouronium salt has formula IC

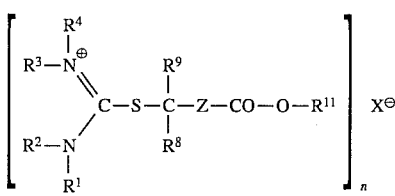

(Ic)

where

R$^1$ to R$^4$, n and X$^\ominus$ are each as defined above; R$^8$ and R$^9$ are each hydrogen or C$_1$–C$_4$-alkyl, R$^{11}$ is hydrogen, C$_1$–C$_{12}$-alkyl, C$_2$–C$_{12}$-alkenyl, C$_2$–C$_{12}$-alkynyl, C$_5$–C$_8$-cycloalkyl, C$_7$–C$_{12}$-phenylalkyl or phenyl which may be substituted by one or two C$_1$–C$_4$-alkyl radicals; and Z is a group of the formula CR$^{12}$=CR$^{13}$— or —C≡C— where R$^{12}$ and R$^{13}$ are each hydrogen or C$_1$–C$_4$-alkyl.

7. The process of claim 1, wherein said thiouronium salt has formula Id

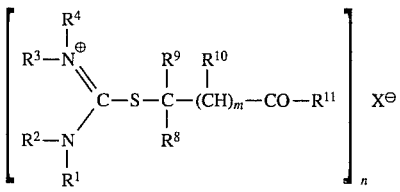

(Id)

where

R$^1$ to R$^4$, n and X$^\ominus$ are each as defined above, R$^8$ to R$^{10}$ are each hydrogen or C$_1$–C$_4$-alkyl, R$^{11}$ is hydrogen, C$_1$–C$_{12}$-alkyl, C$_2$–C$_{12}$-alkenyl, C$_2$–C$_{12}$-alkynyl, C$_5$–C$_8$-cycloalkyl, C$_7$–C$_{12}$-phenylalkyl or phenyl which may be substituted by one or two C$_1$–C$_4$-alkyl radicals, and m is from 0 to 10.

8. The process of claim 1, wherein said thiouronium salt has formula Ie

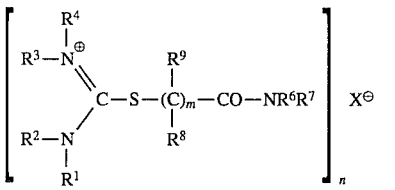

(Ie)

where R$^1$ to R$^4$, R$^6$, R$^7$, n and X$^\ominus$ are each as defined above, R$^8$ and R$^9$ are each hydrogen or C$_1$–C$_4$-alkyl, and m is from 0 to 10.

9. The process of claim 1, wherein said thiouronium salt has formula If

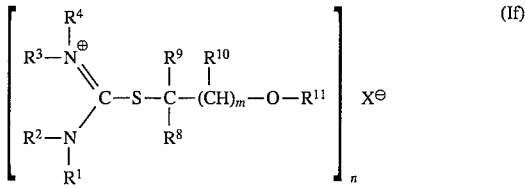

(If)

where R$^1$ to R$^4$, n and X$^\ominus$ are each as defined above, R$^8$ to R$^{10}$ are each hydrogen or C$_1$–C$_4$-alkyl, R$^{11}$ is hydrogen, C$_1$–C$_{12}$-alkyl, C$_2$–C$_{12}$-alkenyl, C$_2$–C$_{12}$-alkynyl, C$_5$–C$_8$-cycloalkyl, C$_7$–C$_{12}$-phenylalkyl or phenyl which may be substituted by one or two C$_1$–C$_4$-alkyl radicals, and m is from 0 to 10.

10. The process of claim 1, wherein said thiouronium salt has formula Ig

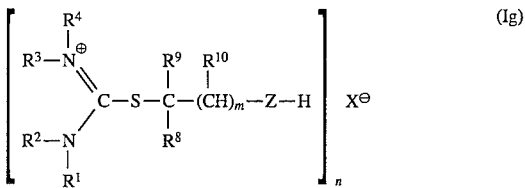

(Ig)

where R$^1$ to R$^4$, n and X$^\ominus$ are eachas defined above, R$^8$ to R$^{10}$ are each hydrogen or C$_1$–C$_4$-alkyl, Z is a group of the formula CR$^{12}$=CR$^{13}$— or —C{C— where R$^{12}$ and R$^{13}$ are each hydrogen or C$_1$–C$_4$-alkyl, and m is from 0 to 10.

11. The process of claim 1, further comprising at least one further brightener.

* * * * *